US00PP33245P2

(12) United States Plant Patent
Janßen

(10) Patent No.: US PP33,245 P2
(45) Date of Patent: Jul. 6, 2021

(54) ***FARGESIA* PLANT NAMED 'JAN W3M'**

(50) Latin Name: ***Fargesia* hybrid**
Varietal Denomination: JAN W3M

(71) Applicant: Wilfried Janßen, Edewecht (DE)

(72) Inventor: Wilfried Janßen, Edewecht (DE)

( * ) Notice: Subject to any disclaimer, the term of this patent is extended or adjusted under 35 U.S.C. 154(b) by 0 days.

(21) Appl. No.: 17/009,617

(22) Filed: Sep. 1, 2020

(51) Int. Cl.
*A01H 5/12* (2018.01)

(52) U.S. Cl.
USPC ..... Plt./384

(58) Field of Classification Search
USPC ..... Plt./384
See application file for complete search history.

(56) References Cited

PUBLICATIONS

PLUTO Plant Variety Database Dec. 23, 2020. p. 1.*

* cited by examiner

*Primary Examiner* — Annette H Para
(74) *Attorney, Agent, or Firm* — Penny J. Aguirre

(57) ABSTRACT

A new cultivar of *Fargesia* plant named 'JAN W3M' that is characterized by its short plant height and a compact plant habit, its leaves that are small in size and dark green in color, and its moderate vigor.

2 Drawing Sheets

Botanical classification: *Fargesia* hybrid.
Variety denomination: 'JAN W3M'.

CROSS REFERENCE TO A RELATED APPLICATIONS

This application is co-pending with a U.S. Plant Patent Application filed for a plant derived from the same breeding program that is entitled *Fergesia* Plant Named 'JAN W3M' (U.S. Plant patent application Ser. No. 17/009,600). This application is also related to a European plant breeders' rights application filed on Jul. 31, 2017, application No. 2017/1896. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Fargesia* of hybrid origin will be referred to hereafter by its cultivar name, 'JAN W3M'. 'JAN W3M' is a new cultivar of bamboo shrub grown for use as a landscape plant.

'JAN W3M' was selected as a single unique plant by the Inventor in a trial field in Edewecht, Germany in 2014 (with numerous seedlings evaluated from 2008 to 2014). The trial field had been planted with seeds from an open pollinated plant of an unnamed and unpatented plant of *Fargesia murieliae* times *Fargesia nitida* from the Inventor's breeding program. The exact male parent is unknown as the seeds were set after open pollination.

Asexual propagation of the new cultivar was first accomplished by the inventor using division in 2014 in Edewecht, Germany. Asexual propagation by division has been determined that the characteristics of 'JAN W3M' are stable and reproduced true to type in successive generations.

SUMMARY OF THE INVENTION

The following traits have been repeatedly observed and represent the characteristics of the new cultivar. These attributes in combination distinguish 'JAN W3M' as a unique cultivar of *Fargesia*.

1. 'JAN W3M' exhibits a short plant height and a compact plant habit.
2. 'JAN W3M' exhibits leaves that are small in size.
3. 'JAN W3M' exhibits leaves that are dark green in color.
4. 'JAN W3M' exhibits moderate vigor.

The female plant of 'JAN W3M' differs from 'JAN W3M' in having a taller plant height (3.5 m), leaves that are larger in size and leaves that are lighter green in color. Typical plant of *Fragesia murieliae* x *Fragesia nitida* differs from 'JAN W3M' in having a much taller plant height 'JAN W3M' can be most closely compared to the cultivars 'Jan 108' (not patented), 'Bimbo' (not patented), and 'JAN W2M'. 'Jan 108' differs from 'JAN W3M' in having a taller plant height, more vigorous growth habit, and leaves that are larger in size and lighter green in color. 'Bimbo' differs from 'JAN W3M' in having a wider spreading plant habit, leaves that are larger in size and lighter green in color, and in not responding as well to pruning. 'JAN W2M' differs from 'JAN W3M' in having a less compact plant habit with a larger plant height and width.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by sites presenting its entrance in the new product showcase at the International Plant Fair "IPM Essen", Bambus Borse, Bambus Heppingsen, Bambus Hecken, Well-born Bamboo Africa, Taspo, Gabot, Bambus-Versand, and Van Vliet New Plants.

BRIEF DESCRIPTION OF THE DRAWINGS

The accompanying colored photographs illustrate the overall appearance and distinct characteristics of the new *Fargesia*. The photographs were taken of a 2-year-old plant as grown outdoors in a polyethylene tunnel in a 27-cm container in Edewecht, Germany.

The photograph in FIG. 1 illustrates the plant habit of 'JAN W3M'.

Figure 1:
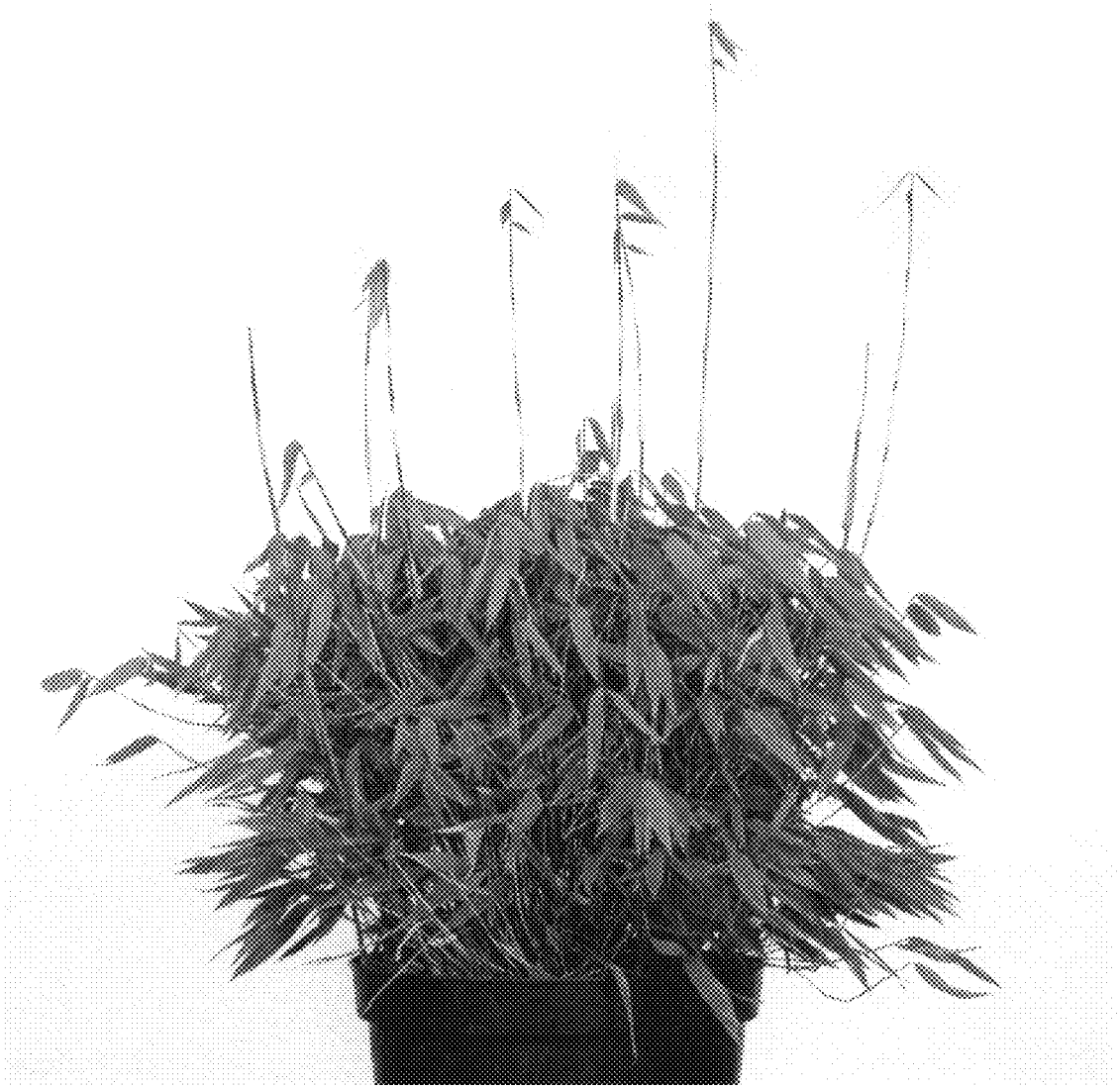
Figure 2:
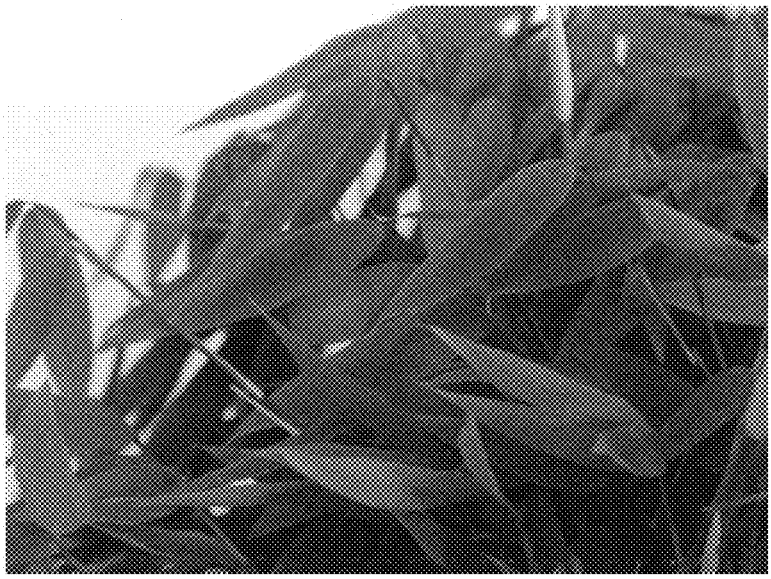

The photograph in FIG. 2 provides a close-up view of the foliage of 'JAN W3M'.

Figure 3:
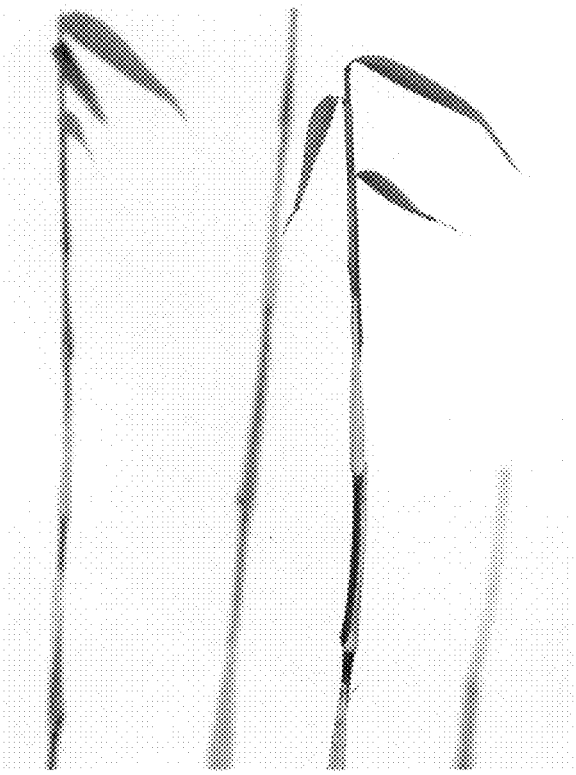

The photograph in FIG. 3 provides a close-up view of the main shoots of 'JAN W3M'.

The colors in the photographs are as close as possible with the digital photography techniques utilized and the color values cited in the detailed botanical description accurately describe the colors of the new *Fargesia*.

DETAILED BOTANICAL DESCRIPTION

The following is a description of 2-year-old plants as grown outdoors in a polyethylene tunnel in 27-cm containers in Edewecht, Germany. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Perennial bamboo.

*Plant habit.*—Compact, obovate in shape, upright stems with dense foliage.

*Height and spread.*—Average of 68.5 cm in length, 61.5 cm in width, fully mature plant reaches an average of 1.5 m in height, 1.2 cm in width when mature in the landscape.

*Cold hardiness.*—At least in U.S.D.A. Zone 5.

*Diseases and pests.*—No resistance or susceptibility to diseases or pests has been observed.

*Root description.*—Fibrous, 199D in color.

*Propagation.*—Division.

*Growth rate.*—Moderate.

*Root development.*—Approximately 1 month after division to root into a small container and 26 weeks from propagation to produce a saleable plant.

Stem description:

*Stem shape.*—Rounded.

*Stem strength.*—Very strong.

*Stem color.*—Young stems; 200A, parts covered with scale leaves; 146C to 146B, mature stems; 144A and 146B, internodes; 146B, older stems and bark; 144A, 146B and 2C.

*Stem size.*—Main branches; average of 44 cm in length, 3 mm in diameter, internodes slightly thicker; 4 mm in diameter, lateral branches; average of 10.2 cm in length, 1 mm in diameter, internodes slightly thicker; 1.5 mm in diameter.

*Stem surface.*—Moderately glossy.

*Stem aspect.*—Near vertical, an average of 80° to horizontal.

*Internode length.*—Main branches; 6.8 cm, lateral branches; 2.2 cm.

*Branching.*—An average of 320 main basal shoots with an average of 4 (ranges from 0 to 16) lateral branches per main shoot.

*Scale leaves.*—Young stems have scale leaves that are dropped as the stems mature; oblanceolate in shape, average of 4.5 cm in length and 9 mm in width, finely praemorse apex, cuneate base, upper surface color; between 161D and 199D, lower surface color; between 161A and 161B.

Foliage description:

*Leaf shape.*—Lanceolate.

*Leaf division.*—Simple.

*Leaf arrangement.*—Alternate, growing at the tips of main and lateral branches.

*Leaf attachment.*—Petiolate.

*Leaf aspect.*—Flat.

*Leaf base.*—Cuneate to rounded.

*Leaf apex.*—Long apiculate.

*Leaf venation.*—Parallel, upper surface color; 143B, lower surface color; 146B.

*Leaf margins.*—Entire.

*Leaf surface.*—Both surfaces smooth, glabrous and non-rugose, upper surface slightly glossy, lower surface matte.

*Leaf size.*—Average of 7 cm in length and 1.3 cm in width.

*Leaf color.*—Young upper surface; 143A and 144A, young lower surface; 138A, mature upper surface; 137A, mature lower surface a color between 137C and 138A.

*Quantity.*—An average of 3 (varying between 2 and 4) per branch.

*Petioles.*—Average of 2 mm in length and 1 mm in diameter, strong, both surfaces are smooth and glabrous, upper surface moderately glossy, lower surface matte, upper surface color 152D in color, lower surface color 153C in color.

Inflorescence description: Does not produce flowers.

It is claimed:

1. A new and distinct cultivar of *Fargesia* plant named 'JAN W3M' as herein illustrated and described.

* * * * *